United States Patent
Kopperschmidt et al.

(10) Patent No.: US 7,985,196 B2
(45) Date of Patent: Jul. 26, 2011

(54) METHOD FOR AT LEAST PARTIALLY DRAINING AN EXTRACORPOREAL BLOOD FLOW AND HAEMODIALYSIS DEVICE FOR USE WITH SAID METHOD

(75) Inventors: Pascal Kopperschmidt, Dittelbrunn (DE); Joachim Noack, Bad Neustadt (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 484 days.

(21) Appl. No.: 12/086,593

(22) PCT Filed: Mar. 6, 2007

(86) PCT No.: PCT/EP2007/001894
§ 371 (c)(1), (2), (4) Date: Jun. 16, 2008

(87) PCT Pub. No.: WO2007/104447
PCT Pub. Date: Sep. 20, 2007

(65) Prior Publication Data
US 2010/0168640 A1 Jul. 1, 2010

(30) Foreign Application Priority Data

Mar. 14, 2006 (DE) .......................... 10 2006 012 087

(51) Int. Cl.
*A61M 37/00* (2006.01)
*C02F 1/44* (2006.01)
(52) U.S. Cl. ............... 604/6.09; 604/5.04; 604/5.01; 604/6.616; 210/645; 210/646
(58) Field of Classification Search ................ 604/4.01, 604/5.01, 5.04, 6.13, 6.09, 6.16; 210/645, 210/646
See application file for complete search history.

(56) References Cited

U.S. PATENT DOCUMENTS

| 4,444,596 A | 4/1984 | Gortz et al. |
| 4,444,597 A * | 4/1984 | Gortz et al. ............ 134/18 |
| 5,336,165 A * | 8/1994 | Twardowski ............ 604/6.1 |

FOREIGN PATENT DOCUMENTS

| DE | 34 42 744 A1 | 6/1986 |
| WO | WO 96/40313 | 12/1996 |
| WO | WO 97/11770 | 4/1997 |
| WO | WO 00/12991 | 3/2000 |
| WO | WO 01/51106 A1 | 7/2001 |

OTHER PUBLICATIONS

Machine translation of DE 3442744.*
English translation of DE 3,442,744 as provided by the USPTO translation service, Nov. 2010.*

* cited by examiner

*Primary Examiner* — Leslie R Deak
(74) *Attorney, Agent, or Firm* — Jacobson Holman PLLC

(57) ABSTRACT

A method and a hemodialysis machine provide for at least partial emptying of an extracorporeal blood circulation after patient blood in the circulation has been returned to the patient via an infusion liquid which displaces the blood. The method includes emptying at least a blood chamber of a hemodialyzer subdivided by a semipermeable membrane into the blood chamber and a dialysis fluid chamber without additionally connecting an arterial blood line and a venous blood line of the circulation to one another. The arterial blood line is actively or passively aerated at a first point and the venous blood line is actively or passively aerated at a second point. The infusion liquid is emptied through the membrane into the dialysis fluid chamber and then via a dialysis fluid discharge line. The method is operable by a control program that runs automatically without requiring any manual input after activation of the program.

15 Claims, 1 Drawing Sheet

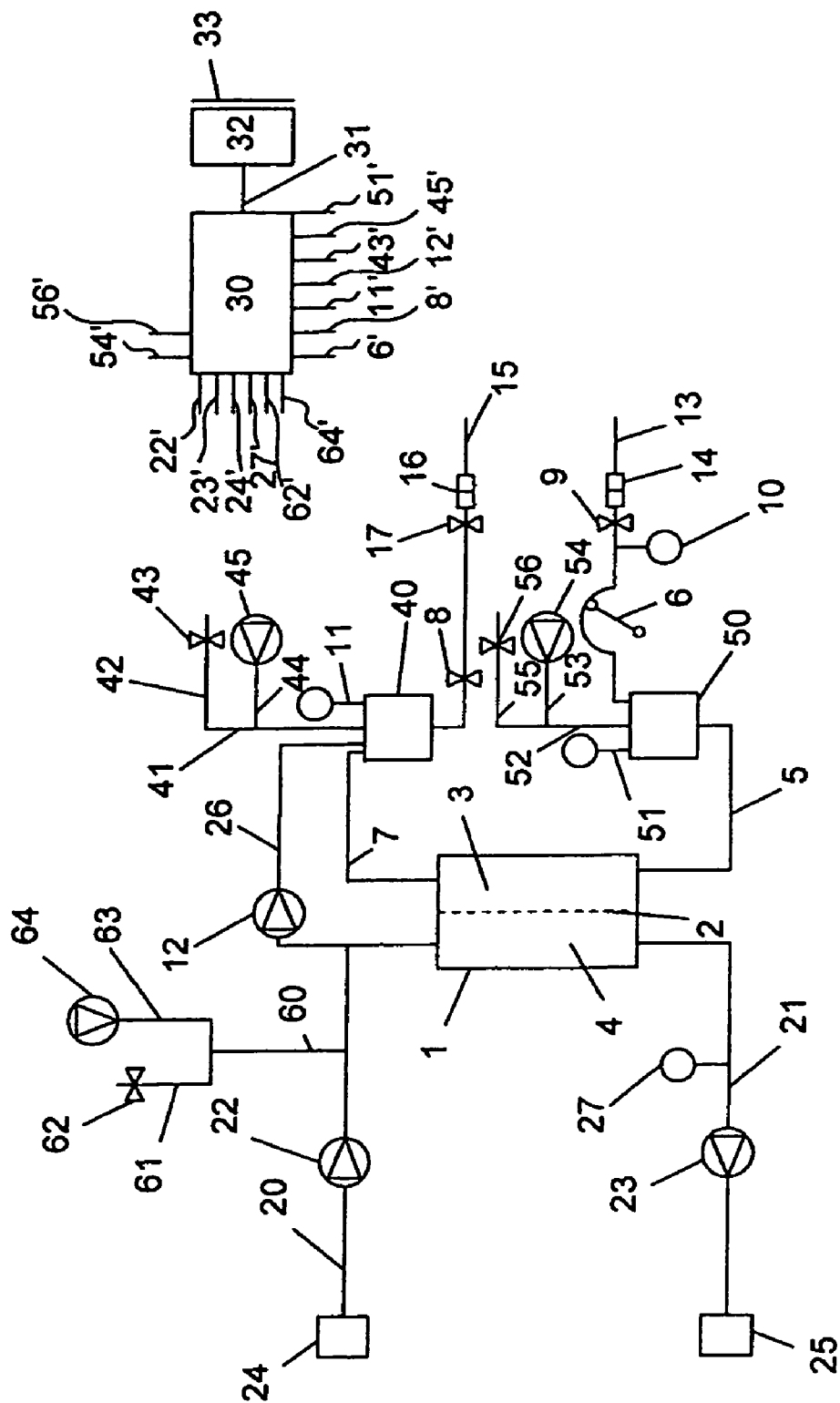

METHOD FOR AT LEAST PARTIALLY DRAINING AN EXTRACORPOREAL BLOOD FLOW AND HAEMODIALYSIS DEVICE FOR USE WITH SAID METHOD

CROSS-REFERENCE TO RELATED APPLICATION

This is a national stage of PCT/EP07/001,894 filed Mar. 6, 2007 and published in German.

BACKGROUND OF THE INVENTION

1. Field of Invention

The invention relates to the field of emptying extracorporeal blood circulations after a hemodialysis treatment.

2. Description of the Prior Art

In a hemodialysis treatment, blood from a patient to be treated circulates in an extracorporeal circulation in which blood flows from a withdrawal point through an arterial blood line to the blood chamber of a hemodialysis machine divided by a semipermeable membrane into a blood chamber and a dialysis fluid chamber and through a venous blood line to a return point. The dialysis fluid chamber is in turn part of a dialysis fluid circulation in which dialysis fluid circulates as cleaning fluid. For this purpose, the commercial hemodialyzers usually have thousands of hollow fibers that have semipermeable walls. Blood flows through the interior of the hollow fibers while the dialysis fluid is fed into the fiber interspace, usually in the opposite direction from the blood, and is carried away. The elements of the extracorporeal blood circulation and the hemodialyzer are often provided only for a single use, whereas the connecting lines of the dialysis fluid circuit are normally reused.

The dialysis fluid has concentrations of blood constituents such as electrolytes corresponding approximately to those of a healthy person, so that the corresponding concentrations in the blood can be kept at a normal level. Substances such as creatinine or urea to be removed from blood are not present in the dialysis fluid, so these are removed from the blood by diffusion simply because of the concentration gradient on the membrane. With the help of a pressure gradient, excess water is withdrawn from the blood by convection and/or ultrafiltration.

Such processes are controlled by hemodialysis machines, which usually also ensure preparation of the dialysis fluid from water and concentrates so that it has the correct composition and temperature. At the same time, this equipment is increasingly capable of assuming a wide variety of monitoring functions of the hemodialysis treatment to minimize the risk to the patient and permit rapid countermeasures to be taken if there are complications.

At the end of the hemodialysis treatment, the extracorporeal blood circulation is first filled with the patient's blood. Since the volume of this blood is usually approximately 200 mL, which is a substantial quantity, this blood is returned to the patient after the end of the treatment. It is customary in this regard to first stop a pump that is arranged in the extracorporeal blood circulation and interrupt the vascular access at the withdrawal point, e.g., by removing the arterial cannula. Then the cannula itself is removed and the remaining arterial connection point is connected to a bag containing a physiological infusion solution, usually saline solution. Then operation of the blood pump is started again and the blood is conveyed back through the return point, which is still connected to the patient, whereupon the extracorporeal blood circulation is filled up with the infusion solution at the same time. If the phase limit between the blood and the infusion solution has reached the return point, the return process is concluded. Then after stopping the blood pump again, the connection of the venous blood line to the patient at the return point can be interrupted, for example, by pulling the venous cannula.

In this condition, the extracorporeal blood circulation is completely filled with fluid. The same thing is true of the dialysis fluid circulation and in particular also the dialysis fluid chamber of the hemodialyzer in which essentially dialysis fluid remains.

To dispose of the components of the extracorporeal circulation and the hemodialyzer, it is advantageous if these components are emptied of the liquid contained in them prior to being discarded. This is true to a particular extent of the two chambers of the hemodialyzer that contain most of the fluid. Emptying reduces the weight of the used disposable item, which is usually classified as special waste, and reduces the problem of pollution of the environment due to the fluid discharged.

WO 96/040313 A1 therefore proposes connecting the extracorporeal blood circulation to an air source of a hemodialysis machine after a disinfection step to replace the fluid with air in this area. In another embodiment, it is also proposed that the dialysis fluid circulation should be emptied by connecting it to the same air source. To empty the extracorporeal blood circulation, however, the arterial blood line must be connected to a disinfection port and the venous blood line must be connected to an outflow port, which necessitates additional operation steps. At the same time, it is important to be sure that there is no contamination of the hydraulics of the hemodialysis machine due to the directly closed extracorporeal blood circulation.

WO 01/051106 A1 describes a method in which the arterial and venous blood lines are not only in fluid connection through the blood chamber of a hemodialyzer but also are connected to form a ring. Fluid contained in the extracorporeal circulation is then circulated in the extracorporeal circulation with the blood pump running and is conveyed through the membrane of the hemodialyzer into the dialysis fluid circulation by a pressure gradient. An aeration opening may be provided on the venous air separator, permitting a resupply of air through an opened valve on reaching a certain suction pressure. This method also requires additional operation steps due to the additional use of the two blood lines and requires the use of other components such as connectors or even line elements.

SUMMARY OF THE INVENTION

The object of the present invention is to improve upon a generic method for emptying the extracorporeal blood circulation after the hemodialysis treatment of a patient to the extent that operation is simplified. This invention is also based on the object of providing a generic hemodialysis machine for use of the inventive method.

According to the teaching of this invention, these objects are achieved by a method and a hemodialysis machine having the features described herein. Advantageous embodiments of the invention are the also described herein.

The invention is based on the observation that emptying of the essential volume component of the extracorporeal blood circulation may already be achieved in a simple manner. To do so, it is sufficient to empty the blood chamber of the hemodialyzer. In this case, additional connection steps are not generally necessary for connecting the arterial and venous blood lines to one another or to special ports. Instead, the emptying method may be started immediately after disconnecting from the patient. With a hemodialysis machine, the inventive method can be automated easily in that a control unit, such as one of those present anyway in most machines of this type, controls the individual process steps after corresponding activation means have been operated. In this way, the operating personnel need only operate an activation means designed as a key for example and the hemodialysis machine performs all the necessary measures automatically. In a refinement of the invention, the dialysis fluid chamber of the hemodialyzer may also be emptied advantageously so that the completely hemodialyzer is emptied after conclusion of the emptying procedure.

The inventive method for at least partial emptying of an extracorporeal blood circulation is used after the blood in the extracorporeal blood circulation is returned to the patient with the help of an infusion fluid which displaces the blood to the patient and the patient is separated from the extracorporeal blood circulation. The extracorporeal circulation includes an arterial blood line leading from an arterial connection point to the blood chamber of the hemodialyzer which is divided by a semipermeable membrane in to a blood chamber and a dialysis fluid chamber, and also includes the blood chamber of the hemodialyzer as well as a venous blood line leading from the blood chamber to a venous connection point. According to this invention, without additionally connecting the arterial and venous connection points to one another, the arterial blood line is actively or passively aerated at a first point and/or the venous blood line is actively or passively aerated at a second point. Then the liquid in the blood chamber of the hemodialyzer and in the section of the arterial blood line between the blood chamber and the first point and/or in the section of the venous blood line between the blood chamber and the second point is emptied through the semipermeable membrane into the dialysis fluid chamber and a dialysis fluid discharge line leaving the chamber.

The first point may be actively or passively aerated by a first aeration means which comprises a first branching line branching off from the first point. Equally, the first point can be actively or passively aerated through a second aeration means comprising a second branching line that branches off from the second point.

For the emptying, a pressure gradient may be created on the semipermeable membrane by suction in the dialysis fluid discharge line leading away from the dialysis fluid chamber.

It is particularly advantageous if the dialysis fluid chamber is actively or passively aerated before, during or after emptying the extracorporeal blood circulation for the additional emptying.

The arterial blood line may be sealed off from the emptying process between the first point and the arterial connection point or at the arterial connection point itself, which is generally accomplished by closing a hose clamp situated on the arterial blood line which is designed as a hose line. Similarly, the venous blood line between the second point and the venous connection point or at the venous connection point itself may be sealed off from the emptying process by a hose clamp. This prevents dripping from the ends of the arterial and venous blood lines.

Since no special operation steps are required according to this invention, the components of the extracorporeal blood circulation on a hemodialysis machine may remain unchanged during the emptying process. In particular, the first and/or second points may be selected so that the blood pumping means, usually furnished as an occluding pump, are arranged in the arterial and/or venous blood lines between the first point and the arterial connection point and/or the second point and the venous connection point. Then the occluding blood pumping means can seal the corresponding blood lines by shutdown during the emptying process. In particular, it is not necessary for the blood pumping means to intervene in the emptying process by conveying blood.

The inventive hemodialysis machine is equipped with means for holding an extracorporeal blood circulation, whereby said extracorporeal blood circulation has an arterial blood line through which a patient's blood can flow from an arterial connection point to the blood chamber of a hemodialyzer divided by a semipermeable membrane into a blood chamber and a dialysis fluid chamber, and also has the blood chamber of the hemodialyzer and a venous blood line through which the blood can be returned from the blood chamber to the patient through a venous connection point. In addition, the hemodialysis machine also includes a dialysis fluid discharge line leading from the dialysis fluid chamber to an outlet. According to this invention, the hemodialysis machine has first aeration means for active or passive aeration at a first point in the arterial blood line and/or second aeration means for active or passive aeration at a second point in the venous blood line and also an emptying activation means and a control unit, the control unit being configured so that after operation of the emptying activation means, the first and/or second aeration means are triggered in such a way that the blood chamber and the arterial line between the first point and the blood chamber and/or the venous line between the second point and the blood chamber can be emptied of fluid through the semipermeable membrane without any additional connection of the arterial blood line to the venous blood line.

The first and/or second aeration means may comprise first and/or second branching lines that branch off from the first and/or second points. For passive aeration, valves may be provided in the branching lines. In the case of active aeration, the branching lines lead to gas pressure sources such as the compressors which are usually present in conventional hemodialysis machines.

The control unit may also be configured in such a way that a pump provided in the dialysis fluid discharge line is triggered to generate a lower pressure in the dialysis fluid chamber in comparison with the blood chamber. Due to this reduced pressure, the fluid present in the extracorporeal circulation is conveyed through the semipermeable membrane of the hemodialyzer into the drain of the hemodialysis machine without requiring any special connections of individual hose ends, e.g., to a ring line.

The hemodialysis machine is advantageously also designed so that it comprises third aeration means connected to the dialysis fluid chamber for active or passive aeration of the dialysis fluid chamber. The control unit in this case may be configured in such a way that by activation of the third aeration means before, during or after emptying of the extracorporeal blood circulation, the dialysis fluid chamber of the hemodialyzer is additionally emptied of fluid.

Blood pumping means, usually present in the form of an occluding pump, may be used for interrupting the extracorporeal blood circulation between the first point and the arterial connection point and/or between the second point and the venous connection point. In this case, the control unit may be designed in such a way that it seals the corresponding blood lines during the emptying process by shutting down the blood pumping means.

Additional details and advantages of the invention are described in greater detail on the basis of an exemplary embodiment of an inventive hemodialysis machine as illustrated schematically in the single drawing FIGURE.

BRIEF DESCRIPTION OF THE DRAWINGS

The drawing FIGURE is a schematic diagram of a hemodialysis machine constructed in accordance with an embodiment of the present invention.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

With the help of the drawing FIGURE, the basic design of the inventive hemodialysis machine will be described first. In hemodialysis, blood is sent through an arterial blood line 5 to a hemodialyzer 1 in an extracorporeal circulation. Blood here is taken from the patient through a cannula or a port 13 which is connected to the arterial blood line 5 with the help of a connector 14. In the hemodialyzer 1, a semipermeable membrane 2, usually designed in the form of multiple hollow fibers, separates a first chamber 3 (blood chamber), which is part of the extracorporeal blood circulation, from a second chamber 4 (dialysis fluid chamber), which is part of a dialysis fluid circulation. Substances to be removed from the blood pass through the semipermeable membrane 2 into the dialysis fluid and are thereby removed. At the same time, an excess amount of fluid from blood can be ultrafiltered via a pressure gradient and removed via the subsequent dialysis fluid. Finally, a reverse diffusion gradient, e.g., for sodium ions may also be used for this to transfer certain substances from the dialysis fluid into the blood.

Blood is conveyed in the arterial blood line 5 through a blood pump 6 designed as a roller pump. Blood leaves the first chamber 3 of the hemodialyzer 1 through a venous blood line 7 to be returned back to the patient. The reinfusion takes place through a cannula or a port 15 which is connected to the venous blood line 7 with a connector 16. A venous cutoff clamp 8, which is provided on the venous blood line 7, can be used to interrupt the return flow of blood in emergencies in particular. Such emergencies may occur, for example, when air in the venous blood line 7 is detected by an air detector (not shown).

An arterial pressure sensor 10 is provided on the arterial blood line 5 and a venous pressure sensor 11 is provided on the venous blood line 7. Additional clamps 9 and 17, usually designed as manually operable hose clamps, may also be provided in both blood lines 5 and 7.

A venous blood chamber 40 is connected to the venous blood line 7 and serves to separate air. A second branch line 41, which is part of a second aeration means, opens into the venous blood chamber 40. The second aeration means also comprises a branch of the line 41 into a line 42 which may be sealed with a valve 43, and to a line 44 into which air can be pumped via a compressor 45. The line 42 can be connected to the environment by opening the valve 43. The second branch line 41 can therefore be aerated passively with the help of the valve 43 or actively with the help of the compressor 45. It is also possible to provide only either the line 42 or the line 44 to allow either only an active or passive aeration. Aeration is performed via sterile filters to prevent contamination of the hemodialysis machine.

Similarly, an arterial blood chamber 50 is connected to the arterial blood line 5. A first branch line 52 branches off from the arterial blood line and is part of a first aeration means and can be passively aerated through a line 55 that can be closed with a valve 56 and can be actively aerated through a line 53 that is connected to a compressor 54. Another pressure sensor 51 may be connected to the arterial blood chamber 50. The arterial blood chamber 50 is often present anyway with a so-called single-needle treatment in which the two connectors 14 and 16 are joined in the form of a Y piece, and the patient's blood is removed and returned through a single cannula in alternation. In this case, another blood pump (not shown) may also be provided in the arterial blood line 5 downstream from the arterial blood chamber 50.

It is also possible for there to be no arterial chamber, for only first or only second aeration means to be provided or for the first and/or second branch lines to branch off at T-type connecting pieces.

The second chamber 4 of the hemodialyzer has dialysis fluid flowing through it, this fluid being supplied through a dialysis fluid inlet line 20 from a dialysis fluid preparation unit 24 and removed through a dialysis fluid discharge line 21 to an outlet 25. The dialysis fluid is circulated via delivery and balancing equipment 22 and 23, whereby the exact amount of any ultrafiltrate to be removed can be determined. Those skilled in the art will have access to various designs for implementation of the delivery and balancing equipment 22 and 23, so that no details need be provided at this point. This is also true of providing dialysis fluid through the dialysis fluid preparation unit 24. Reference is made to a balancing chamber system as described in U.S. Pat. No. 4,267,040 as an example.

A third branch line 60, which is part of a third aeration means, branches off from the dialysis fluid supply line 20. In a manner similar to the aeration means of the extracorporeal blood circulation, the third branch line 60 also branches into a line 61 that is closable by a valve 62 for passive aeration and a line 63 that is connected to a compressor 64 for active aeration. Again in this case, of course as an alternative, there may also be only the option of passive or active aeration.

For use of actuators and sensors in a hemodialysis machine, those skilled in the art will in general have numerous options available, although they need not be described in detail here. The diagram in the drawing FIGURE is limited to a few of these elements which are sufficient for explanation of the invention.

The hemodialysis machine is controlled and monitored by a control unit 30. To do so, the control unit 30 is connected to the individual actuators and sensors of the machine having signal lines. For the actuators and sensors illustrated in the drawing FIGURE, this is indicated by reference numerals having an apostrophe next to the reference numeral for the respective actuator or sensor; for the sake of simplicity, this is indicated only for the control unit 30.

The control unit 30 is connected to an input and output unit 32 via a data line 31. The input and output unit 32 comprises a display screen 33 designed as a touch screen. Information reported by the control unit 30 is displayed on the touchscreen and at the same time data input by an operating person via the touchscreen is forwarded to the control unit 30.

A substituate line 26 which opens into the blood return line 7 branches off from the dialysis fluid supply line 20. A substituate pump 12 for conveying dialysis fluid as a substituate into the extracorporeal circulation of the hemodialysis machine is provided in the substituate line 26 and is controlled by the control unit 30.

The hemodialysis machine shown in the drawing FIGURE can be used for strict hemodialysis if the substitute pump 12 is deactivated. A hemofiltration treatment can be performed if the dialysis fluid line 20 is interrupted between the branch of the substitute line 26 and the second chamber 4 by a valve (not shown), and a hemodiafiltration treatment can be performed with simultaneous hemodialysis and hemofiltration. Filters (not shown in detail here) can be provided in the dialysis fluid inlet line 20 and/or the substitute line 26 for sterile filtration of the dialysis fluid, to which end a variety of options are available to those skilled in the art. The arrangement of the device may also be such that only a hemodialysis treatment or a hemofiltration treatment is possible. Finally, it is also possible that in the case of a hemofiltration or hemodiafiltration treatment, the substitute may be obtained from a different source than the dialysis fluid.

Before the inventive process is used after a blood treatment, first the cannula 13 connected to the arterial blood line must be separated from the patient when the blood pump 6 is stopped, whereby the line may be sealed off by the hose clamp 9 to prevent dripping. Then the arterial blood line 5 is connected to a bag containing physiological saline solution either directly with the cannula 13 or with the connector 14 as the arterial connection point. With the help of the blood pump 6 which is then operated, with the clamp 9, if present, having been opened again, saline solution is conveyed through the extracorporeal circulation, whereby the blood present there is conveyed back to the patient through the venous cannula 15. If the phase boundary between blood and saline solution has reached the venous cannula 15, the blood pump 6 is stopped again, so that the patient can now also be separated from the venous blood line 7. First, the venous clamp 8 of the hemodialysis machine or the hose clamp 17 can be closed off to prevent the line from dripping.

For the use of the inventive method, the control unit 30 of the inventive hemodialysis machine has initially also stopped the delivery devices 22 and 23 in the dialysis fluid circulation. For initiation of the process, the operating personnel need operate only one emptying activation means which is provided as a button, for example, on the display screen 33. No additional measures are necessary. In particular, no line segments need be connected directly or indirectly via additional line parts.

Then the control unit 30 triggers the compressor 45 or the valve 43 of the second aeration means to deliver blood into the venous blood line 7 at the branch to the first branch line 41 or cause blood to flow in there. At the same time, the compressor 54 or the valve 56 of the first aeration means is triggered to deliver air into the arterial blood line 5 at the branch to the first branch line 52 or to cause air to flow in there.

In addition, the control unit 30 triggers the delivery means 23 in the dialysis fluid discharge line 21 to convey fluid to the outlet 25. The dialysis fluid supply line 20 is kept closed by the stopping the delivery unit 22 or by a valve (not shown here). The valve 62 and the compressor 64 are also sealed and/or out of operation. Due to the pressure gradient on the semipermeable membrane 2, which is established by the delivery means 23, the saline solution in the extracorporeal circulation flows into the dialysis fluid circulation and is conveyed to the outlet 25. At the same time, replenishing air flows through the opened valves 43 and 56 to replenish displaced air. If the compressors 45 and 54 are to be operated, the pressure gradient on the membrane 2 is increased further. In this case, the delivery means 23 may also be turned off if their design allows through-flow. In this way, the extracorporeal circulation between the arterial blood chamber as the first point and the venous blood chamber as the second point is emptied of fluid.

The emptying process can be monitored via the pressure sensors 11, 51 or 27. In the case of passive aeration, this results in the following: when the emptying of the blood chamber 3 is concluded, the air remaining there cannot pass through the membranes in the case of the hydrophilic membranes 2 conventionally used today. After emptying the blood chamber 3, this leads to a pressure drop in the dialysis fluid chamber 4, which can be detected by the pressure sensor 27. The pressure sensor could also be situated upstream in the dialysis fluid supply line 20 as long as this area is in pressure connection with the dialysis fluid chamber 4. However, if the aeration is actively performed with the help of the compressors, then after successfully emptying the blood chamber 3, there is a rise in pressure in the emptied area, which can be detected by the pressure sensors 11 or 51. Instead of pressure values, the power values of the compressors or of the delivery means 23 may equally be used as the comparative parameter. It is also possible to operate the aeration means with a time delay after the buildup of the pressure gradient on the membrane or as a function of the measured pressure values of the pressure sensors 11, 27 or 51. The active or passive aeration could thus be initiated only when the pressure falls below a predetermined pressure limit.

After emptying the blood chamber 3, the first aeration means on the arterial blood line 5 and the second aeration means on the venous blood line 7 are deactivated by the control unit, i.e., the valves 43 and 56 are closed or the compressors 45 and 56 are turned off, so there is no longer any connection to the environment.

Although the emptying of the blood chamber 3 or the hemodialyzer 1 already entails a mentionable reduction in the weight of the disposable parts of the extracorporeal circulation, the emptying program is still not concluded in a particularly advantageous embodiment of the invention. In this case, automatic emptying of the dialysis fluid chamber 4 also follows the emptying of the blood chamber 3 of the hemodialyzer 1. The control unit also further activates the delivery means 23 and allows passive aeration of a part of the dialysis fluid circulation by opening the valve 62 or active aeration by turning on the compressor 64. Again in this case, a time-delayed or pressure-controlled aeration may be used.

The end of the emptying program can be detected by the pressure sensor 27 if it is situated downstream from the dialysis fluid chamber in this case. As soon as only air is present at this point in the dialysis fluid discharge line, a certain suction pressure or delivery pressure can no longer be maintained. Alternatively, an electric conductivity cell, which is usually present in the dialysis fluid discharge line anyway, or an optical sensor (not shown) may be used to detect the penetration of air to this point and thus detect the end of the emptying process.

The control unit 30 then switches all pumps off and/or closes the corresponding valves and signals to the operating personnel the end of the emptying process with the help of the input and output unit 32. The disposable components of the extracorporeal circulation comprising the arterial blood line 5, the venous blood line 7 and the hemodialyzer 1, which is now completely emptied, can now be removed from the corresponding holding devices on the hemodialysis machine and discarded.

The invention allows simple emptying of the blood chamber of a hemodialyzer, in particular after a hemodialysis treatment. The inventive method may take place here through a control program that runs automatically in the control unit of a hemodialysis machine without requiring any special operation steps by the operation personnel. The operating person is relieved and faulty operation is prevented. At the same time, the weight of disposable components prior to their disposal is reduced.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A method for at least partial emptying of an extracorporeal blood circulation after blood of a patient in the extracorporeal blood circulation has been returned to the patient via an infusion liquid which displaces the blood, and the patient has been separated from the extracorporeal blood circulation, the extracorporeal blood circulation having a hemodialyzer divided by a semipermeable membrane into a blood chamber and a dialysis fluid chamber, with an arterial blood line leading from an arterial connection point to the blood chamber and a venous blood line leading from the blood chamber to a venous connection point, the method comprising:

without additionally connecting the arterial and venous blood lines together, a step of actively or passively aerating the arterial blood line at a first point and the venous blood line at a second point so as to move the infusion liquid in the blood chamber and in a section of the arterial blood line between the blood chamber and the first point and in a section of the venous blood line between the blood chamber and the second point through the semipermeable membrane and into the dialysis fluid chamber for emptying through a dialysis fluid discharge line that exits therefrom.

2. The method according to claim 1, wherein the first point is actively or passively aerated by a first aeration means that includes a first branch line branching off from the first point.

3. The method according to claim 1, wherein the second point is actively or passively aerated by a second aeration means that includes a second branch line branching off from the second point.

4. The method according to claim 1, wherein to effect the emptying, a pressure gradient is generated on the semipermeable membrane by applying a suction in the dialysis fluid discharge line.

5. The method according to claim 1, further comprising actively or passively aerating the dialysis fluid chamber for additional emptying before, during, or after the emptying of the extracorporeal blood circulation.

6. The method according to claim 1, wherein the arterial blood line is sealed off between the first point and the arterial connection point, or at the arterial connection point, itself before the emptying occurs.

7. The method according to claim 1, wherein the venous blood line is sealed off between the first point and the venous connection point, or at the venous connection point, before the emptying occurs.

8. The method according to claim 1, wherein occluding blood pumping means are provided in at least one of the arterial blood line and the venous blood line between the first point and the arterial connection point and the second point and the venous connection point, and the occluding blood pumping means seals off the corresponding blood lines by shutting down before the emptying occurs.

9. A hemodialysis machine that provides for at least partial emptying of an extracorporeal blood circulation after blood of a patient in the extracorporeal blood circulation has been returned to the patient via an infusion liquid which displaces the blood, and the patient has been separated from the extracorporeal blood circulation, comprising:

an extracorporeal blood circulation including a hemodialyzer divided by a semipermeable membrane into a blood chamber and a dialysis fluid chamber, with an arterial blood line leading from an arterial connection point to the patient to the blood chamber, and a venous blood line leading from the blood chamber to a venous connection point to the patient;

a dialysis fluid discharge line leading from the dialysis fluid chamber to an outlet;

first aeration means for active or passive aeration at a first point in the arterial blood line and a second aeration means for active or passive aeration at a second point in the venous blood line;

an emptying activation means; and a control unit that triggers the first and the second aeration means after operation of the emptying activation means so as to empty of fluid, through the semipermeable membrane, (i) the blood chamber, (ii) the arterial blood line between the first point and the blood chamber, and (iii) the venous blood line between the second point and the blood chamber, without any additional connection of the arterial blood line to the venous blood line.

10. The hemodialysis machine according to claim 9, wherein the first aeration means includes a branch line branching off from the first point, the branch line having a valve disposed therein that is openable so as to passively aerate the first point, and the second aeration means includes a branch line branching off from the second point, the branch line having a valve disposed therein that is openable so as to passively aerate the second point.

11. The hemodialysis machine according to claim 9, wherein the first aeration means includes a branch line branching off from the first point, the branch line being connected to a gas excess pressure source configured to actively aerate the first point, and the second aeration means includes a branch line branching off from the second point, the branch line being connected to a gas excess pressure source configured to actively aerate the second point.

12. The hemodialysis machine according to claim 9, further comprising a pump provided in the dialysis fluid discharge line, wherein the control unit is configured to trigger the pump to generate a lower pressure in the dialysis fluid chamber than in the blood chamber.

13. The hemodialysis machine according to claim 9, further comprising a third aeration means connected to the dialysis fluid chamber for active or passive aeration thereof, wherein the control unit is configured to empty the dialysis fluid chamber of fluid by activation of the third aeration means before, during, or after the emptying of the extracorporeal blood circulation.

14. The hemodialysis machine according to claim 9, further comprising an occluding blood pumping means for conveying fluid in at least one of the arterial blood line and the venous blood line between the first point and the arterial connection point, and the second point and the venous connection point, wherein the control unit is configured to activate the occluding blood pumping means to seal off the corresponding blood lines by shutting down before the emptying occurs.

15. The hemodialysis machine according to claim 9, further comprising a device that applies a suction to the dialysis fluid discharge line so as to generate a pressure gradient across the semipermeable membrane.

* * * * *

UNITED STATES PATENT AND TRADEMARK OFFICE
CERTIFICATE OF CORRECTION

PATENT NO. : 7,985,196 B2
APPLICATION NO. : 12/086593
DATED : July 26, 2011
INVENTOR(S) : Kopperschmidt et al.

It is certified that error appears in the above-identified patent and that said Letters Patent is hereby corrected as shown below:

In the claims:

Col. 9, line 50 delete "itself".

Signed and Sealed this
Fifth Day of November, 2013

Teresa Stanek Rea
*Deputy Director of the United States Patent and Trademark Office*